US 8,073,215 B2

(12) United States Patent
Lu et al.

(10) Patent No.: US 8,073,215 B2
(45) Date of Patent: Dec. 6, 2011

(54) AUTOMATED DETECTION OF PLANES FROM THREE-DIMENSIONAL ECHOCARDIOGRAPHIC DATA

(75) Inventors: Xiaoguang Lu, Plainsboro, NJ (US); Bogdan Georgescu, Plainsboro, NJ (US); Yefeng Zheng, Dayton, NJ (US); Joanne Otsuki, Oakland, CA (US); Dorin Comaniciu, Princeton Junction, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 791 days.

(21) Appl. No.: 12/186,815

(22) Filed: Aug. 6, 2008

(65) Prior Publication Data
US 2009/0074280 A1    Mar. 19, 2009

Related U.S. Application Data

(60) Provisional application No. 60/973,217, filed on Sep. 18, 2007, provisional application No. 60/974,935, filed on Sep. 25, 2007.

(51) Int. Cl.
G06K 9/00    (2006.01)
(52) U.S. Cl. ..................................... 382/128
(58) Field of Classification Search ........... 382/128–134
See application file for complete search history.

(56) References Cited

U.S. PATENT DOCUMENTS

| | | | | |
|---|---|---|---|---|
| 7,916,919 B2 * | 3/2011 | Zheng et al. | ................ | 382/131 |
| 2006/0034513 A1 | 2/2006 | Cai et al. | | |
| 2006/0064017 A1 | 3/2006 | Krishnan et al. | | |
| 2006/0239527 A1 | 10/2006 | Krishnan et al. | | |
| 2007/0071295 A1 | 3/2007 | Jackson | | |
| 2008/0009722 A1 | 1/2008 | Simopoulos et al. | | |

OTHER PUBLICATIONS

Freeman, William T., and Edward H. Adelson. "The Design and Use of Steerable Features." IEEE Trans. Patt. Anal. and Machine Intell. 13.9 (1991): 891-906. Web.*
Zheng et al., "Fast Automatic Heart Chamber Ssegmentation from 3D CT Data Using Marginal Space Learning and Steerable Features", Proc. International Conference on computer Vision, 2007.
Zhuowen Tu, "Probabilistic Boosting-Tree: Learning Discriminative Models for Classification, Recognition, and Clustering", Proc. International Conference on Computer Vision, pp. 1589-1596, 2005.
Xiagoguang Lu et al., "AUTOMPR: Automatic Detection of Standard Planes in 3D Echocardiography", Proc. IEEE Int'l Symp. on Biomedical Imaging (ISBI '08), pp. 1279-1282, May 2008.
F. Sheehan, E. Bolson, R. Martin, G. Bashein, and J. McDonald, "Quantitative three-dimensional echocardiography: Methodology, validation and clinical applications," in *Proc. MICCAI*, Boston, MA, 1998, pp. 102-109.
A. Giachetti, "On-line analysis of echocardiographic image sequences," *Medical Image Analysis*, vol. 2, No. 3, pp. 261-284, 1998.

(Continued)

*Primary Examiner* — Clayton E Laballe
*Assistant Examiner* — Dennis Hancock

(57) ABSTRACT

A plane position for a standard view is detected from three-dimensional echocardiographic data. The position of the plane within the volume is defined by translation, orientation (rotation), and/or scale. Possible positions are detected and other possible positions are ruled out. The classification of the possible positions occurs sequentially by translation, then orientation, and then scale. The sequential process may limit calculations required to identify the plane position for a desired view.

20 Claims, 3 Drawing Sheets

OTHER PUBLICATIONS

X. Papadimetris, A. Sinusas, D. Dione, and J. Duncan, "3D cardiac deformation from ultrasound images," *in Proc. MIC-CAI*, Cambridge, U.K., 1999, pp. 420-429.

G. Jacob, A. Noble, M. Mulet-Parada, and A. Blake, "Evaluating a robust contour tracker on echocardiographic sequences," *Medical Image Analysis*, vol. 3, No. 1, pp. 63-76, 1999.

L.D. Jacobs, I.S. Salgo, S. Goonewardena, L. Weinert, P. Coon, D. Bardo, O. Gerard, P. Allain, J.L. Zamorano, L.P. de Isla, V. Mor-Avi, and R.M. Lang, "Rapid online quantification of left ventricular volume from real-time three-dimensional echocardiographic data," *European Heart Journal*, vol. 27, No. 4, pp. 460-468, 2006.

Harvey Feigenbaum, William F. Armstrong, and Thomas Ryan, *Feigenbaum's echocardiography*, Lippincott Williams & Wilkins, 2005.

Gerardo I. Sanchez-Ortiz, Gabriel J. T. Wright, Nigel Clarke, Jrme Declerck, Adrian P. Banning, and J. Alison Noble, "Automated 3-D echocardiography analysis compared with manual delineations and SPECT MUGA," *IEEE Trans. on Medical Imaging*, vol. 21, No. 9, pp. 1069-1076, 2002.

B. Georgescu, X. Zhou, D. Comaniciu, and A. Gupta, "Database-guided segmentation of anatomical structures with complex appearance," in *Proc. IEEE CVPR*, 2005.

P. Viola and M. J. Jones, "Robust real-time face detection," *International Journal of Computer Vision*, vol. 57, No. 2, pp. 137-154, 2004.

* cited by examiner

AUTOMATED DETECTION OF PLANES FROM THREE-DIMENSIONAL ECHOCARDIOGRAPHIC DATA

RELATED APPLICATIONS

The present patent document claims the benefit of the filing date under 35 U.S.C. §119(e) of Provisional U.S. Patent Application Ser. Nos. 60/973,217, filed Sep. 18, 2007, and 60/974,935, filed Sep. 25, 2007, which are hereby incorporated by reference.

BACKGROUND

The present embodiments relate to medical diagnostic ultrasound imaging. In particular, views of desired planes are extracted from echocardiographic data representing a volume.

Three-dimensional (3D) ultrasound imaging systems are used for 3D echocardiography. 3D echocardiography allows evaluation of both morphology and pathology. Research studies have shown that 3D analysis provides more precise information about the pathophysiology of the heart than conventional analysis of two-dimensional (2D) views and is of particular help for volume and ejection fraction (EF) calculation. However, interpretation and quantitative analysis of the 3D volumetric data is more complex and time consuming than that of conventional two-dimensional (2D) echocardiography. Detection of anatomical structures in 3D volumetric data may allow better analysis, but may be used less for diagnosis due to complexity.

Standard views are used to visualize cardiac structures and are the starting point of many echocardiographic examinations. For example, all four chambers, i.e., left and right ventricles, and left and right atria, are present in the apical four chamber (A4C) view. In the apical three chamber (A3C) view, the left ventricle, the left atrium, and the aorta are present. In a 3D volume, such views can be re-constructed as multiplanar reformatted/reconstruction (MPR) planes. Finding the standard 2D planes in a 3D volume may improve consistency among users and may be used to adjust acquisition parameters for better image quality.

Although 3D echocardiographic volumes provide much richer information about a heart than 2D echocardiographic images, a heart can be located in different positions with various orientations within each volume. It is time consuming for users to navigate through a 3D volume to search the target structure. A major barrier for using 3D echocardiography for quantitative analysis of heart function in routine clinical practice is the absence of accurate and robust detection methods necessary to make the analysis automatic. In addition to the ultrasound operator's capability, other factors including transducer selection, instrument settings, patient comfort and positioning, the configuration of the scan, and the patient's breathing pattern may affect the quality of the ultrasound images or data for analysis. This leads to large appearance variations and inconsistent image qualities, which makes the automatic detection task much more difficult.

BRIEF SUMMARY

By way of introduction, the preferred embodiments described below include methods, computer readable media and systems for detection of a plane from three-dimensional echocardiographic data. The position of the plane within the volume is defined by translation, orientation (rotation), and/or scale. Possible positions for a desired view are detected and other possible positions are ruled out. The classification of the possible positions occurs sequentially by translation, then orientation, and then scale. The sequential process may limit calculations required to identify the plane position for a desired view. For classification, features are calculated from data representing a plane within the volume. These planar or other features are used by machine-learnt classifiers to detect the position of one or more desired views.

In a first aspect, a method is provided for detection of a plane from three-dimensional echocardiographic data. A sequence of machine-trained classifiers is applied to the three-dimensional echocardiographic data. A first of the classifiers is for translation of the plane within a volume represented by the three-dimensional echocardiographic data. A second of the classifiers is for rotation of the plane within the volume. A third of the classifiers is for scale of the plane within the volume. A position of the plane is detected as a function of the output of the first, second, and third classifiers. An image is generated as a function of the position of the plane.

In a second aspect, a computer readable storage medium has stored therein data representing instructions executable by a programmed processor for detecting standard view planes in a volume represented by three-dimensional echocardiographic data. The storage medium includes instructions for calculating features for each of a plurality of possible plane positions within the volume, at least one of the features calculated only from the data representing the possible plane position within the volume, detecting the standard view planes with respective classifiers as a function of the features, and generating images from the data for the standard view planes.

In a third aspect, a system is provided for detecting plane positions for standard planes of a multiplanar reconstruction of a heart volume. A memory is operable to store ultrasound data representing the heart volume. A processor is operable to calculate first planar features for each of a plurality of translated plane positions, rule out hypotheses corresponding to the translated plane positions with a translation classifier and as a function of the first planar features, leaving first remaining hypotheses, to calculate second planar features for each of a plurality of rotated plane positions associated with the first remaining hypotheses, rule out hypotheses corresponding to the rotated plane positions with an orientation classifier and as a function of the second planar features, leaving second remaining hypotheses, to calculate third planar features for each of a plurality of scaled planes associated with the second remaining hypotheses, rule out hypotheses corresponding to the scaled planes with a scale classifier and as a function of the third planar features, leaving at least one third remaining hypothesis, and to determine the plane position of one of the standard planes as a function of the at least one third remaining hypothesis. A display is operable to display an image of the one of the standard planes as a function of the plane position.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the FIG. 1 is a block diagram of one embodiment of a medical ultrasound imaging system.

DETAILED DESCRIPTION OF THE DRAWINGS AND PRESENTLY PREFERRED EMBODIMENTS

An automated supervised learning method detects standard or other multiplanar reformatted planes (MPRs) from a 3D echocardiographic volume in order to achieve fast, accurate, and consistent MPR detection. For example, a computer detects six major or standard MPR planes: A4C-apical four-chamber plane; A2C-apical two chamber plane; A3C-apical three chamber plane; SAXB-short axis basal plane; SAXM-short axis middle plane; and SAXA-short axis apex plane. Automatic detection may allow automation of the clinical workflow and facilitate subsequent processing tasks, such as endocardial wall motion analysis.

Figure 1:
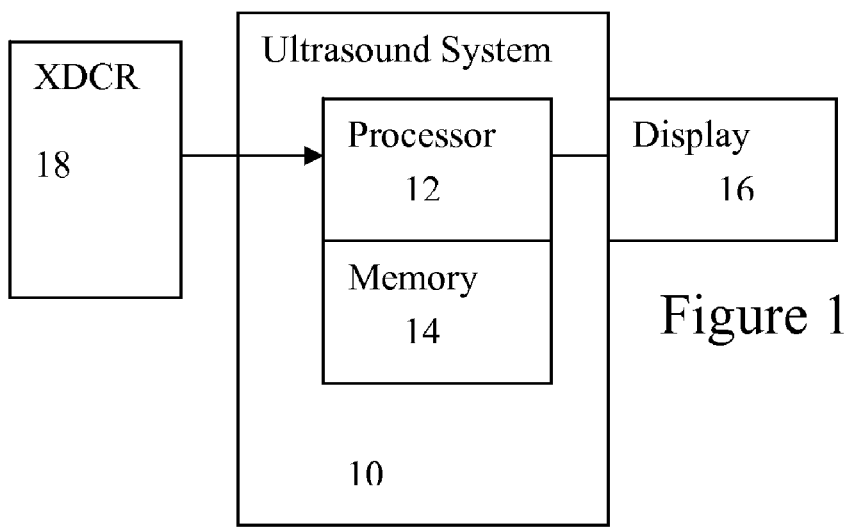

FIG. 1 shows a medical diagnostic imaging system 10 for detecting a plane position of a desired view. Plane detection may provide multi-planar reconstruction from ultrasound volume data. The system 10 is a medical diagnostic ultrasound imaging system, but may be a computer, workstation, database, server, or other system.

The system 10 includes a processor 12, a memory 14, a display 16, and a transducer 18. Additional, different, or fewer components may be provided. For example, the system 10 includes a transmit beamformer, receive beamformer, B-mode detector, Doppler detector, harmonic response detector, contrast agent detector, scan converter, filter, combinations thereof, or other now known or later developed medical diagnostic ultrasound system components. As another example, the transducer 18 is not provided, such as where the system 10 is a workstation for off-line or later detection of one or more desired 2D views within a volume.

The transducer 18 is a piezoelectric or capacitive device operable to convert between acoustic and electrical energy. The transducer 18 is an array of elements, such as a multi-dimensional or two-dimensional array. Alternatively, the transducer 18 is a wobbler for mechanical scanning in one dimension and electrical scanning in another dimension.

The system 10 uses the transducer 18 to scan a volume. Electrical and/or mechanical steering allows transmission and reception along different scan lines in the volume. Any scan pattern may be used. In one embodiment, the transmit beam is wide enough for reception along a plurality of scan lines. In another embodiment, a plane, collimated or diverging transmit waveform is provided for reception along a plurality, large number, or all scan lines.

Ultrasound data representing a volume is provided in response to the scanning. The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format.

The memory 14 is a buffer, cache, RAM, removable media, hard drive, magnetic, optical, database, or other now known or later developed memory. The memory 14 is a single device or group of two or more devices. The memory 14 is shown within the system 10, but may be outside or remote from other components of the system 10.

The memory 14 stores the ultrasound data, such as ultrasound data representing a heart volume. The heart volume is a volume including at least a portion of the heart. The memory 14 stores flow (e.g., velocity, energy or both) and/or B-mode ultrasound data. Alternatively, the medical image data is transferred to the processor 12 from another device. The medical image data is a three-dimensional data set, or a sequence of such sets. The data represents a three-dimensional region. Any format may be used, such as voxels interpolated to a three-dimensional grid or data representing parallel or non-parallel planes.

For real-time imaging, the ultrasound data bypasses the memory 14, is temporarily stored in the memory 14, or is loaded from the memory 14. Real-time imaging may allow delay of a fraction of seconds, or even seconds, between acquisition of data and imaging. For example, real-time imaging is provided by generating the images substantially simultaneously with the acquisition of the data by scanning. While scanning to acquire a next or subsequent set of data, images are generated for a previous set of data. The imaging occurs during the same imaging session used to acquire the data. The amount of delay between acquisition and imaging for real-time operation may vary, such as a greater delay for initially locating planes of a multi-planar reconstruction with less delay for subsequent imaging. In alternative embodiments, the ultrasound data is stored in the memory 14 from a previous imaging session and used for generating the multi-planar reconstruction without concurrent acquisition.

The memory 14 is additionally or alternatively a computer readable storage medium with processing instructions. The memory 14 stores data representing instructions executable by the programmed processor 12 for detecting standard view planes in a volume represented by three-dimensional echocardiographic data and/or multi-planar reconstruction for ultrasound volume data. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 12 is a general processor, digital signal processor, three-dimensional data processor, graphics processing unit, application specific integrated circuit, field programmable gate array, digital circuit, analog circuit, combinations thereof, or other now known or later developed device for processing medical image data. The processor 12 is a single device, a plurality of devices, or a network. For more than one device, parallel or sequential division of processing may be used. Different devices making up the processor 12 may perform different functions, such as a scanning controller and an image generator operating separately. In one embodiment, the processor 12 is a control processor or other processor of a medical diagnostic imaging system, such as a medical diagnostic ultrasound imaging system processor. The processor 12 operates pursuant to stored instructions to perform various acts described herein, such as obtaining data, detecting standard views, and/or controlling imaging.

In one embodiment, the processor 12 receives acquired ultrasound data during or after scanning and determines locations of one or more planes relative to the volume represented by the data. The processor 12 performs or controls other components to perform the methods described herein.

The processor 12 performs machine learning and/or applies a machine-learnt algorithm. For application, the processor 12 calculates features for sequential classification. The detection algorithm implemented by the processor 12 searches through multiple hypotheses to identify the ones with high probabilities. Multiple hypotheses are maintained between algorithm stages. Each stage, such as a translation stage, an orientation stage, and a scale stage, quickly removes false hypotheses remaining from any earlier stages. The correct or remaining hypotheses propagate to the final stage. Only one hypothesis is selected as the final detection result or a plane position is detected from information for a combination of hypotheses (e.g., average of the remaining hypotheses after the final stage).

The same or different features are used for classification in each stage. For example in a translation stage, features are calculated for each of a plurality of translated plane positions. Using a machine-trained translation classifier, the features are used to rule out hypotheses corresponding to the translated plane positions, leaving a subset of remaining hypotheses.

The features are three-dimensional features. 3D Data enclosing a plane, i.e., a sub-volume, is used to calculate the features. Alternatively, volume data may be interpolated to a plane, and the resulting data representing the plane is used, without other data, to calculate the feature.

Any features may be used. Different types of features may be used for the same classifier, or all of the features are of a same type for a given classifier. In one embodiment, Haar wavelet-like features are calculated. Haar wavelet-like features represent the difference between different portions of a region. Any number of features may be used, such as tens, hundreds, or thousands. The machine learning process may operate to determine a desired subset or set of features to be used for a given classification task.

Feature values are calculated for each hypothesis. For translation classification, the features are calculated for each of the possible translated plane positions. The same features, such as the same Haar functions, are calculated for each of the possible translated plane positions. The translation classifier outputs a probability of a given possible plane position being the correct or desired view based on the feature values. If the probability is above a threshold, the associated hypothesis is maintained If the probability is below a threshold, the associated hypothesis is ruled out and discarded from the pool of hypotheses.

By ruling out one or more hypotheses, the number of possible plane positions associated with rotation may be limited. For example, ruling out one hypothesis and leaving two hypotheses allows the orientation classifier to calculate features for different rotations relative to two different translations instead of three.

The processor 12 calculates the same or different planar and/or other features for each of a plurality of rotated plane positions associated with the remaining hypotheses. Hypotheses corresponding to the rotated plane positions are ruled out with an orientation classifier and as a function of the planar or other features. After application of the orientation classifier, a further subset of hypotheses remains. The remaining hypotheses are for sufficient translations having at least one sufficient rotation.

The processor 12 calculates the same or different planar and/or other features for each of a plurality of scaled planes associated with hypotheses remaining after translation and orientation testing. A scale classifier rules out hypotheses corresponding to the scaled planes as a function of the features. After ruling out none, one or more hypotheses, a remaining set of hypotheses remains for the plane being detected.

In one embodiment, the type of features used for the orientation and scale classifiers are gradient features. For example, the "steerable" features described by Zheng, et al. in "Fast Automatic Heart Chamber Segmentation from 3D CT Data Using Marginal Space Learning and Steerable Features," Proc. Int'l Conf. on Computer Vision, pp. 1-8, 2007, are used. Other types of features may alternatively or additionally be used. The features are volumetric.

Any classifier may be applied, such as a model-based classifier or a learned classifier (e.g., classifier based on machine learning). For learned classifiers, binary or multi-class classifiers may be used, such as Bayesian or neural network classifiers. In one embodiment, a binary boosting classifier with a tree and cascade structure is used. The classifier is instructions, a matrix, a learned code, or other software and/or hardware for distinguishing between information in a medical image. The translation, orientation, and scale classifiers may be the same or different types of classifiers.

In one embodiment, the translation classifier, orientation classifier, and scale classifier are a machine-trained probabilistic boosting tree. Each classifier is constructed as a tree structure. In an alternative embodiment, the non-sequential processing is provided, such as independent classification for translation, orientation and scale or such as a single classifier for classifying based on all possible positions, including scale.

The machine-trained probabilistic boosting tree is trained for the one of the standard planes. The processor 12 is operable to implement different machine-trained probabilistic boosting tree classifiers for different ones of the standard planes.

The processor 12 determines the plane position of one of the standard or other planes as a function of the remaining hypotheses. The detected view is a common or standard view (e.g., apical four chamber, apical two chamber, left parasternal, or sub-coastal), but other views may be recognized. The output of the classifier, such as the probabilistic boosting tree, is used to determine the plane position. The plane position associated with a highest probability is selected. In another embodiment, more than one of the plane positions remaining as hypotheses are selected and combined. For example, an average translation, orientation, and scale of the remaining hypotheses are calculated. The average is the plane position for the desired view.

The display 16 is a CRT, LCD, plasma, projector, printer, or other output device for showing an image. The display 16 displays an image of the detected plane, such as an image of the detected standard plane (e.g., A4C). The data representing the volume is used for generating the image. Data from the volume dataset adjacent to or intersected by the detected plane is used to generate a cut-plane or multiplanar reconstruction image.

Figure 2:
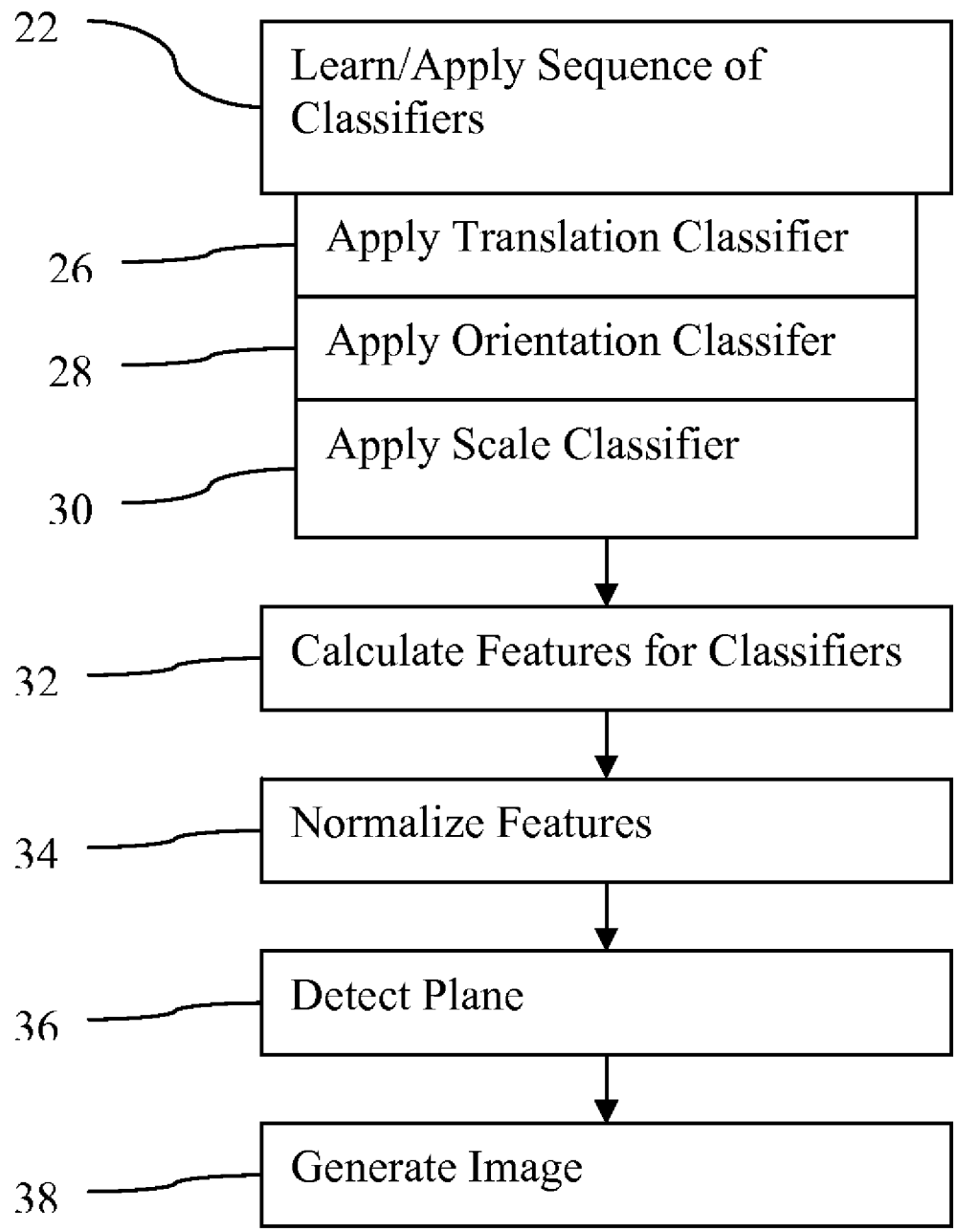
FIG. 2 is a flow chart diagram of embodiments of a method for detection of a plane from three-dimensional echocardiographic data.

FIG. 2 shows a method for detection of a plane, such as a standard multi-planar reconstruction plane, from three-dimensional echocardiographic data. The method is implemented by a medical diagnostic imaging system, a review station, a workstation, a computer, a PACS station, a server, combinations thereof, or other device for image processing medical ultrasound data. For example, the system or computer readable media shown in FIG. 1 implements the method, but other systems may be used.

The method is implemented in the order shown or a different order. Additional, different, or fewer acts may be performed. For example, acts 34 and/or 38 are optional. As another example, sequential classification is not provided, such that sequential or even separate performance of acts 24, 26, and 28 is not provided.

The acts are performed in real-time, such as during scanning. The user may view images of act 38 while scanning to acquire another dataset representing the volume. The images may be associated with previous performance of acts 22-38 in the same imaging session, but with different volume data. For example, acts 22-38 are performed for an initial scan and for subsequent scans during the same imaging session. Multiplanar reconstruction images may be provided in seconds, such as 2 or fewer seconds.

One or more sets of data are obtained. The ultrasound data corresponds to a data set interpolated to a regular 3D grid, displayed images (e.g., detected and scan converted ultrasound data), beamformed data, detected data, and/or scan converted data. The ultrasound data represents a volume or 3D region of a patient. The region includes tissue, fluid or other structures. Different structures or types of structures react to the acoustic energy differently. For example, heart muscle tissue moves, but slowly as compared to fluid. The temporal reaction may result in different velocity or flow data. The shape of a structure or spatial aspect may be reflected in B-mode data. One or more objects, such as the heart, an organ, a vessel, fluid chamber, clot, lesion, muscle, and/or tissue are within the volume region. The data represents the region.

In act 22, a sequence of machine-trained classifiers is learned and/or applied to the three-dimensional echocardiographic data. Each desired plane, such as standard MPR planes are considered, not only in an abstract 2D domain, but a 3D volume sample. Plane detection estimates the pose parameters (i.e., position) for desired each plane. The pose parameters of a 3D rigid body may include 9 components: 3 translations (x; y; z), 3 orientations (e.g., Euler angles w.r.t. for each axis), and 3 scales (one for each axis). One or more of the parameters may not be used, such as not providing scale or only providing scale along one axis.

Searching in a high-resolution 3D volume is prohibitive for online applications or rapid determination. For example, a volume of 100×100×100 voxels has $10^6$ hypotheses for translation. If combining orientation and scale, a combinatorial hypothesis search space expands dramatically. A limited set of hypotheses may be used based on any desired criteria, such as relative expected positions of different planes. By training a series of detectors that estimate plane or pose parameters at a number of sequential stages, the number of calculations may be reduced. The stages are applied in the order of complexity as the parameter degrees of freedom increase (e.g., translation, then orientation, and then scale), but other orders may be used. For example, scale may be adjusted only along two axes given a translation and orientation. In other embodiments, other learning with or without hierarchical searching is used.

Any classifier or classifiers may be used. The classifier may be a model or detector using imaging processing, filtering, or other techniques. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used.

The classifier is trained from a training data set using a computer. In one embodiment, the classifier is a knowledge-based probabilistic model, such as marginal space learning using a hierarchical search. A database of known cases is collected for machine learning, providing a database-driven knowledge-based approach. For training data, three-dimensional context information is preserved and guides the detection process. Knowledge is embedded in large annotated data repositories where expert clinicians manually indicate the standard MPR planes. The known cases are spatially aligned or registered, such as by aligning the coordinate system to the identified A4C view. The detectors are trained on a large number of annotated 3D echocardiographic volumes.

For an optional pyramid data structure, the training sets are selected for the detectors at different levels depending on the complexity of the detection task. At the coarse level, the negative plane positions are far from the positive plane positions and randomly sampled across reasonable plane configurations while maintaining a relatively large gap (e.g., any empirically determined spacing) from the positives. At the fine level, negatives are selected only within an empirically determined neighborhood of the positives in accordance to the search strategy, while decreasing the gap in between as compared to the coarse level.

Figure 3:
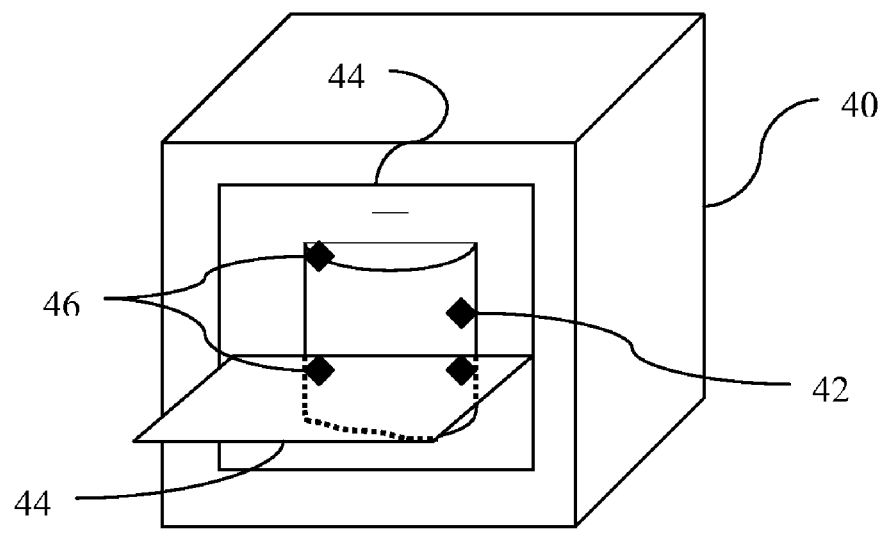
FIG. 3 is a graphical representation of a volume region, object, and associated planes of a multi-planar reconstruction in one embodiment.
Figure 4:
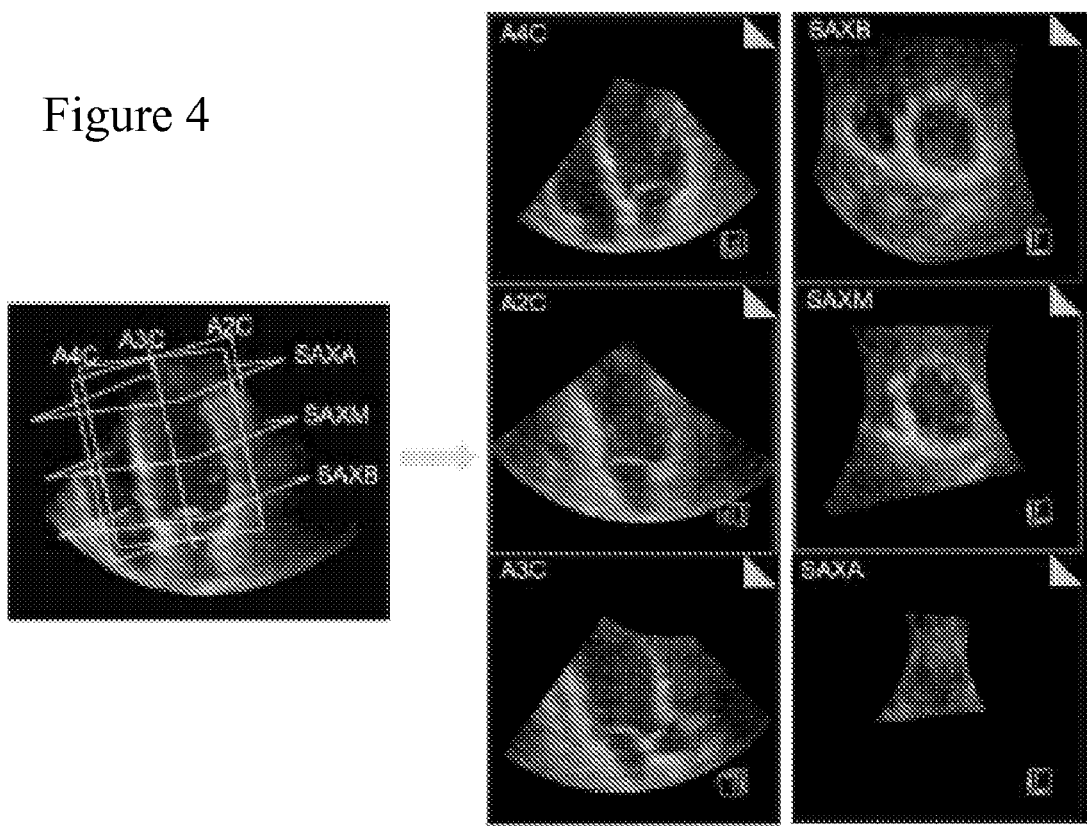
FIG. 4 shows example medical images of standard echocardiographic views and represents the relative plane positions for the views.

FIGS. 3 and 4 shows example volumes with planes 44. The learned algorithm uses the learned model to search for targets (MPR planes) in the hypothesis space. The classifier learns various feature vectors for distinguishing between a desired plane and planes not being detected. In alternative embodiments, the classifier is manually programmed.

For learning-based approaches, the classifier is taught to distinguish based on features. For example, the probability model algorithm selectively combines features into a strong committee of weak learners based on Haar-like local rectangle filters whose rapid computation is enabled by the use of an integral image. Features that are relevant to the MPRs are extracted and learned in a machine algorithm based on the experts' annotations, resulting in a probabilistic model for MPRs. A large pool of features may be extracted. The training determines the most determinative features for a given classification and discards non-determinative features.

Volumetric or planar features may be used with the 3D echocardiographic data. In one embodiment, planar features are provided. The features are calculated from data representing a plane. The same features are calculated for each possible position of a given plane. Different combinations of features may be used for detecting different planes and/or plane parameters. For example, different sequential classification stages utilize different features computed from the 3D volume data. Each classifier selects a set of discriminative features that are used to distinguish the positive target from negatives. The features are selected from a large pool of features. The large pool is determined by a programmer or may include features systematically determined.

For the classifiers at the translation stage, Haar wavelet-like features are used, but other features may be provided. Haar wavelet-like features are calculated efficiently using integral image-based techniques. For classifiers at the rotation and scale stages, gradient or steerable features are used, but other features may be provided Steerable features constitute a flexible framework, where a few points are sampled from the volume under a special pattern (e.g., a regular grid). A few local features are extracted for each sampling point, such as voxel intensity and gradient. To evaluate the steerable features under a specified orientation, the sampling pattern is controlled, and no computationally expensive volume rotation is involved. The computation of steerable features does not require volume rotation and re-scaling, which are computationally expensive.

A tree structure may be learned and may offer efficiency in both training and application. Often, in the midst of boosting a multi-class classifier, one class (or several classes) has been completely separated from the remaining ones and further boosting yields no additional improvement in terms of the classification accuracy. For efficient training, a tree structure is trained. To take advantage of this fact, a tree structure is trained by focusing on the remaining classes to improve learning efficiency. Posterior probabilities or known distributions may be computed, such as by correlating anterior probabilities together.

To handle the background classes with many examples, a cascade training procedure may be used. A cascade of boosted binary-class strong classifiers may result. The cascade of classifiers provides a unified algorithm able to detect and classify multiple objects while rejecting the background classes. The cascade structure corresponds to a degenerate decision tree. Such a scenario presents an unbalanced nature of data samples. The background class has voluminous samples because all data points not belonging to the object classes belong to the background class. Alternatively, the classifiers are sequentially trained without cascade.

A probabilistic boosting tree (PBT), which unifies classification, recognition, and clustering into one treatment, may be used. For example, the translation, orientation, and scale classifiers are trained as a probabilistic boosting tree. A probabilistic boosting tree is learned for each plane of interest. The classifier is a tree-based structure with which the posterior probabilities of the presence of the plane of interest are calculated from given data. Each plane detector not only provides a binary decision for a given sample, but also a confidence value associated with the decision. The nodes in the tree are constructed by a combination of simple classifiers using boosting techniques, such as disclosed by Tu, "Probabilistic Boosting-Tree: Learning Discriminative Models for Classification, Recognition, and Clustering," Proc. Int'l Conf. on Computer Vision, pp 1589-1596, 2005.

Any probabilistic tree structure may be used. In one embodiment, the translation stage applied in act 26 is a binary tree using Haar wavelet features. Three levels are provided where each node contains 20 weak classifiers. Each classifier is based on one feature. The orientation stage applied in act 28 is a binary tree using gradient or steerable features. Six levels are provided where each node contains 40 weak classifiers. The scale stage applied in act 30 is a binary tree using gradient or steerable features. Seven levels are provided where each node contains 40 weak classifiers. The final probabilistic boosting tree probability is calculated as a weighted sum of all the probabilities from the leaf nodes that a given sample has traversed. Additional or different features, classifiers, levels, types of features, combination of probabilities, or types of trees may be used. For example, the scale classifier is not provided or applied.

To apply the classifier, features are calculated in act 32. The features are calculated for each of the possible plane positions. Other features may be calculated regardless of the possible plane position, such as where a feature for a sub-volume may be determinative in combination with planar features for a possible plane position.

For each possible plane position, the features for a given classification are calculated. For the translation stage, the possible plane positions relate to different positions translated along three axes. For example, Haar features are calculated for classifying whether a given translation possible plane position may be the desired plane. For the rotation stage, the possible plane positions relate to rotation about the three axes at remaining translation positions. For the scale stage, the possible plane positions relate to different size regions at the remaining rotation and translation positions. Different features may be calculated for different stages. Different features may be calculated for different views being detected.

The features are calculated from the echocardiographic data representing the volume. In one embodiment, features are calculated from the data at different resolutions. A volume pyramid is provided, such that the data set is down sampled to different resolutions. For example, one set of data has fine resolution, such as the scan resolution, and another set of data has a coarse resolution, such as the fine set decimated by ¼ in each dimension (i.e., down sample by a factor of 4). The sets represent the same object in the same volume. Any number (one, two, or more) sets may be used. Features are calculated from a coarse set and then in a fine set of the volume pyramid. The machine learning may determine the determinative features. For each determinative feature, a data set at the corresponding resolution is provided.

The sets are in any format, such as Cartesian or polar coordinate. In one embodiment, the ultrasound data is acquired in an acoustic (e.g., polar) coordinate format, and the Cartesian or display space is populated in real time with only visible surfaces or selected planes. In another embodiment using a scan converter, processor, or graphics processing unit, real-time conversion from the acoustic space to the Cartesian or display space is provided. The ultrasound data is processed in the Cartesian space (e.g., 3D grid) to orient the multi-planar reconstruction.

In act 34, at least one of the features is normalized. Due to inconsistent imaging conditions of ultrasound in real applications, the features within each sample may be normalized. Any normalization function may be used, such as normalizing by an average of a database of examples for a given plane position. In one embodiment, the features are normalized by the data used to calculate the feature. For example, a Haar feature is calculated from data representing an entire plane. The data of the plane or region is averaged. The average is subtracted from the Haar feature value and the result is divided by the standard deviation of the data from the plane or region. Other or no normalization may be used. For example, the steerable or gradient features for the orientation and scale stages are not normalized.

In act 36, a position of a plane is detected. The position associated with the desired view is detected. For example, one or more standard view planes are detected as a function of the output of the classifiers. The features are used to determine the most likely position of the plane for the view. The plane detectors are discriminative classifiers trained on the 3D echocardiographic volumes. The plane detector determines if a given sub-volume sample (data for a possible plane position) is positive or negative. Positive and negative samples correspond to correct and incorrect plane parameters (positions), respectively.

For sequential detection to limit complexity or increase efficiency, a plane position for one view is detected by sequential translation, orientation and scale detection. The classifier rules out possible plane positions by sequentially calculating the features for translated possible plane positions, for rotated possible plane positions, and for scaled possible plane positions. Each stage removes possible plane positions from a hypotheses list.

First, features are calculated for different possible plane positions. The different possible plane positions correspond to translation along different axes. Any step size or search strategy may be used, such as a coarse search with a fine search at the locations identified as likely in the coarse search. The detector provides a probability for each possible position. The possible positions associated with sufficient probability are maintained in the hypotheses pool. Sufficient probability is determined by a threshold, by selecting the top X (where X is one or more) probabilities, or other test.

For the orientation detector, the locations of the planes to be rotated are the possible plane positions remaining after application of the translation classifier. For each sufficient translation position, different rotations are tested. Any angle step size and/or search strategy may be used. The orientation detector identifies sufficient plane positions associated with different rotations. If no rotation position for a given translation position is sufficient, the translation position is dropped from the hypothesis pool.

The scale detector applies different scale factors for the possible plane positions remaining after translation and orientation detection. Any step size and/or search strategy may be used for scaling. If no scale for a given plane position is sufficient, the plane position is dropped from the hypothesis pool. The remaining plane positions and corresponding scales are sufficient according to the translation, orientation, and scale classifiers.

The detected view is the possible plane position with the highest probability output by the scale classifier. Alternatively, the detected view is the possible plane position with the highest average probability from the translation, orientation, and scale detectors. In other embodiments, an average position of the remaining sufficient possible plane positions is determined. The average position is the detected view. Other limitations may be used, such as averaging the position of the top Y most possible plane positions.

One or more planes are detected. For example, the positions of the planes for standard echocardiography views are determined. An apical two chamber view, an apical four chamber view, an apical three chamber view, a parastemal long axis view, and/or a parasternal short axis view are determined. For example, FIGS. 3 and 4 show a volume region 40 with an object 42 at least partly within the region 40. The object 42 may have any orientation within the volume region 40. The position of planes 44 relative to the volume is determined for multi-planar reconstruction. Other standard or non-standard views may be determined. Standard views may be standard for the medical community or standard for an institution. Predetermined views include non-standard views, such as a pre-defined view for clinical testing.

Different classifiers are machine trained for the different standard views. Any combination of classifiers may be used. Each classifier is applied to determine the corresponding plane position independent of the output of other classifiers. Alternatively, the output of one classifier is used for detection of another plane. In one embodiment to detect two or more (e.g., 6 standard) planes, a coarse-to-fine strategy is applied through a multi-scale hierarchy. A position of an apical four chamber view is detected with a down sampled set of the data (e.g., ¼ resolution). Because the target MPR planes have anatomic regularities with each other and with respect to the left ventricle (LV), an initial position of the possible plane positions for the other views is set based on the A4C plane position. An A4C detector is learned and applied at a coarse level in a low-resolution volume. Other views may be detected for the original or base position.

The plane position for the A4C view is used to limit the search region for fine or coarse plane parameter estimation. An initial position of another of the standard view planes is determined as a function of the position of the A4C view. The initial plane parameters (position, orientation, and scale) for other views (e.g., A2C, A3C, SAXB, SAXM, and SAXA) with respect to the A4C view are based on empirical statistics. For example, the average relative position from the training data set is used. The initial position sets the search region. The possible plane positions may be limited in translation, rotation, and/or scale relative to the initial position.

The other standard view planes are detected using the volume data and the search space limited by the initial position. Since the initial position limits the search space, higher resolution data may be used. At higher resolutions, a plane detector for more accurate parameter estimation trained for each plane is applied to search the best candidate only in a small neighborhood around their initial detection results. A different or the same A4C detector may be applied to the fine dataset to refine the A4C position.

In act 38, an image is generated as a function of the detected plane position. Images are generated for each of the determined views. Data corresponding to the position of the plane is extracted from the volume. The data is used to generate an image for the view. For example, multi-planar reconstruction images are generated from the ultrasound data. The planes define the data to be used for imaging. Data associated with locations intersecting each plane or adjacent to each plane is used to generate a two-dimensional image. Data may be interpolated to provide spatial alignment to the plane, or a nearest neighbor selection may be used. The resulting images are generated as a function of the orientation of the multi-planar reconstruction and provide the desired views. The images represent different planes 44 through the volume region 40.

In one embodiment, specific views are generated. All or a sub-set of the specific views are generated. Where planes corresponding to the views are identified, the views may be provided. For example, all the available standard or predetermined views in ultrasound data representing a region are provided. The images for each view may be labeled (e.g., A4C) and/or annotated (e.g., valve highlighted). Fewer than all available views may be provided, such as displaying no more than three views and having a priority list of views.

In one example embodiment, 326 echocardiographic volume sequences are collected. For each sequence, the end diastole (ED) frame (a 3D volume) is extracted and added into an experimental database. In total, there are 326 3D echocardiographic volumes in the database. For each volume, six standard planes (A4C, A2C, A3C, SAXB, SAXM, and SAXA) are manually annotated by clinical experts and used as ground truth for evaluation.

To measure the difference between two planes, two error metrics are applied, i.e., angle and distance. The angle between two planes is defined as the angle between two plane normals. The distance between two planes is measured as the distance of an anchor on one plane to the other plane, where the anchor is the LV center (for A4C, A3C, A2C, and SAXM) or the intersection between the LV long axis and the MPR (for SAXB and SAXA). Based on the ground truth annotations, the LV long axis is computed as the average of the two intersections of A4C-C and A4C-A3C, and the LV center is calculated as the intersection between the LV long axis and SAXM.

A 4-fold cross-validation scheme is applied for evaluation. The entire dataset of 326 volumes is randomly partitioned into four quarters. For each experiment, three quarters (244 volumes) were combined for training and the remaining one quarter (82 volumes) was used as unseen data for testing.

In total, there are four experiments so that each volume has been used once for testing. Automatic MPR performance is summarized based on all 4 folds and provided in Table 1 below. MPRs in 3D echocardiography data present ambiguities due to data quality, leading to difficulties for accurate identification. Preliminary intra-user variability analysis yields an average angle error of about 8.2 degrees and average distance error of about 3.2 mm.

| (a) Overall performance | | |
|---|---|---|
| | Avg. angle error | Avg. distance error |
| mean | 11.3 | 3.7 |
| std | 8.0 | 2.1 |
| median | 9.3 | 3.3 |

| (b) Performance breakdown (apical planes) | | | | | | |
|---|---|---|---|---|---|---|
| | A4C | | A2C | | A3C | |
| | Angle | Dist. | Angle | Dist. | Angle | Dist. |
| mean | 13.2 | 3.5 | 15.2 | 2.9 | 14.5 | 3.4 |
| std | 12.5 | 3.4 | 13.0 | 2.8 | 13.2 | 3.9 |
| median | 10.4 | 2.7 | 11.6 | 2.2 | 10.9 | 2.3 |

| (c) Performance breakdown (short axis planes) | | | | | | |
|---|---|---|---|---|---|---|
| | SAXB | | SAXM | | SAXA | |
| | Angle | Dist. | Angle | Dist. | Angle | Dist. |
| mean | 8.2 | 3.6 | 8.2 | 4.3 | 8.2 | 4.5 |
| std | 6.2 | 3.1 | 6.2 | 3.5 | 6.2 | 3.5 |
| median | 6.8 | 2.9 | 6.8 | 3.7 | 6.9 | 3.7 |

This automated system may significantly reduce the burden of searching anatomic structures for human echocardiography examiners across a large variety of different volumes. With the detected standard MPRs, advanced quantitative analysis can proceed automatically, such as ejection fraction analysis.

In another embodiment, Anchor-Based methods and systems are provided for automatic plane detection from 3D echocardiography data. Accurate and robust detection of anatomic structures may allow for automatic quantitative analysis of heart function in routine clinical practice of 3D echocardiography. Standard planes are the starting point of many clinical examinations. In the anchor-based approach, standard multiplanar reformatted reconstruction (MPR) planes are detected from a 3D echocardiographic volume, with plane orientation inferred from the anchors without searching the large orientation space.

Because three non-collinear points are sufficient to determine a plane in three-dimensional space, instead of searching the orientation space, detected anchors are used to infer the orientation of the target plane. The same strategy can be applied to estimate the scale of anatomic structures of interest.

A plane is represented as a point (p) on the plane and the normal of the plane (n). Given three detected anchors ($p_1$, $p_2$, and $p_3$) on a plane, the plane parameters (p, n) can be calculated as follows:

$$n = (p_3 - p_1) \times (p_2 - p_1),$$

$$p = (p_1 + p_2 + p_3)/3, \text{ (or any point on the plane)}$$

where × denotes cross product.

Anchors are detected from 3D volumes using a database-driven knowledge-based approach. Knowledge is learned through extensive volume data training repositories, in which expert clinicians reliably annotate standard MPR planes through knowledge-based approaches along with anchors that have anatomic meanings. MPR planes share common features. For three major apical MPR planes (i.e., A4C, A2C, and A3C), expert clinicians annotate 7 anchors in total, namely apex, basal inferoseptal point, basal anterolateral point, basal inferior point, basal anterior point, basal inferolateral point, and basal anteroseptal point. For example, the A4C plane can be determined by the apex, basal inferoseptal point, and basal anterolateral point. Although three non-collinear anchors are the minimum requirement to determine a plane, more anchors along with a plane fitting algorithm and/or anchor selection schemes can be applied to enhance inference robustness against noise and outliers.

A model/detector is learned for each anchor. The anchor detector is trained on a large set of registered 3D echocardiographic volumes, which are used to determine if a given sub-volume sample is positive or negative. Positive samples are the sub-volume centered at the target anchors, while negatives are selected by extracting sub-volumes that are away from the positive samples with a pre-defined margin in the translation space.

A probabilistic boosting tree (PBT) or other algorithm is used to construct each anchor detector. Different algorithms may be used for different anchors. In one example, the classifier is a tree-based structure with which posterior probabilities of the presence of the anchor are calculated from given data. Each anchor detector not only provides a binary decision for a given sample, but also a confidence value associated with the decision. The nodes in the tree are constructed by a nonlinear combination of simple classifiers using boosting techniques.

Each anchor detector selects a set of discriminative features that are used to distinguish the target anchor from negatives from a large pool of features. Haar wavelet-like features, which construct an over-complete feature pool and can be efficiently calculated using integral image-based techniques, are used, but other features may be used. Due to inconsistent imaging conditions of ultrasound in real applications, the features within each sample may be normalized, such as by subtracting the average and divide by the standard deviation.

An online detection algorithm applies the models to detect anchors and uses the detected anchors to infer the target MPR planes. For each anchor, only translation parameters need to be estimated in order to infer the MPR planes, which dramatically reduces the parameter search space (no orientation).

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for detection of a plane from three-dimensional echocardiographic data, the method comprising:

applying a sequence of machine trained classifiers to the three-dimensional echocardiographic data, a first of the classifiers for translation of the plane within a volume represented by the three-dimensional echocardiographic data, a second of the classifiers for rotation of the plane within the volume, and a third of the classifiers for scale of the plane within the volume;

detecting a position of the plane as a function of the output of the first, second, and third classifiers; and generating an image as a function of the position of the plane.

2. The method of claim 1 wherein the first, second, and third classifiers comprise a probabilistic boosting tree.

3. The method of claim 1 wherein the first, second, and third classifiers receive inputs of features calculated from the three-dimensional echocardiographic data and each removes possible plane positions from a hypotheses list, the position being a function of at least one possible plane position remaining after application of the first, second, and third classifiers.

4. The method of claim 1 wherein the first classifier identifies a first plurality of possible positions, the second classifier identifies a second plurality of possible positions as a function of the first plurality, and the third classifier identifies a third plurality of possible positions as a function of the second plurality, the position of the plane being a function of the third plurality.

5. The method of claim 4 wherein the position of the plane is an average of the possible positions of the third plurality.

6. The method of claim 1 wherein the first, second, and third classifiers operate with features, the features being volumetric features for possible positions of the plane.

7. The method of claim 1 wherein the first classifier operates with Haar wavelet features.

8. The method of claim 1 wherein the second and third classifiers operate with gradient features.

9. The method of claim 1 further comprising normalizing features of at least the first classifier.

10. The method of claim 1 wherein the position of the plane comprises a standard echocardiography view from the group of an apical two chamber view, an apical four chamber view, an apical three chamber view, a parasternal long axis view, and a parasternal short axis view;

further comprising:

determining positions of other standard echocardiography planes using different machine-trained classifiers.

11. The method of claim 1 wherein applying comprises identifying a plurality of features from the data in a first coarse set and in a second fine set of a volume pyramid.

12. In a non-transitory computer readably storage medium having stored therein data representing instructions executable by a programmed processor for detecting standard view planes in a volume represented by three-dimensional echocardiographic data, the storage medium comprising instructions for:

calculating features for each of a plurality of possible plane positions within the volume, at least one of the features calculated only from the data representing the possible plane position within the volume;

detecting the standard view planes with respective classifiers as a function of the features; and generating images from the data for the standard view planes.

13. The computer readable media of claim 12 wherein the calculating features comprises calculating different features for different standard views and wherein the respective classifiers comprise classifiers machine trained for the different standard views.

14. The computer readable media of claim 12 wherein, for a first of the standard view planes, the respective classifier rules out possible plane positions by sequentially calculating the features for translated possible plane positions, for rotated possible plane positions, and for scaled possible plane positions.

15. The computer readable media of claim 12 wherein calculating features comprises calculating gradient features.

16. The computer readable media of claim 12 further comprising instructions for normalizing at least one of the features as a function of the data used to calculate the feature.

17. The computer readable media of claim 12 wherein a position of an apical four chamber view is detected with a down sampled set of the data, wherein an initial position of another of the standard view planes is determined as a function of the position, and wherein detecting comprises detecting the other of the standard view planes from the data and with a search space limited by the initial position.

18. A system for detecting plane positions for standard planes of a multiplanar reconstruction of a heart volume, the system comprising:

a memory operable to store ultrasound data representing the heart volume;

a processor operable to calculate first features for each of a plurality of translated plane positions, rule out hypotheses corresponding to the translated plane positions with a translation classifier and as a function of the first features, leaving first remaining hypotheses, to calculate second features for each of a plurality of rotated plane positions associated with the first remaining hypotheses, rule out hypotheses corresponding to the rotated plane positions with an orientation classifier and as a function of the second features, leaving second remaining hypotheses, to calculate third features for each of a plurality of scaled planes associated with the second remaining hypotheses, rule out hypotheses corresponding to the scaled planes with a scale classifier and as a function of the third features, leaving at least one third remaining hypothesis, and to determine the plane position of one of the standard planes as a function of the at least one third remaining hypothesis; and a display operable to display an image of the one of the standard planes as a function of the plane position.

19. The system of claim 18 wherein the translation classifier, orientation classifier, and scale classifier comprise a machine-trained probabilistic boosting tree for the one of the standard planes and wherein the processor is operable to implement different machine-trained probabilistic boosting tree classifiers for different ones of the standard planes.

20. The system of claim 18 wherein the first features comprise Haar features calculated from data representing planes corresponding to the translated plane positions, and wherein the second and third features comprise steerable features.

* * * * *